(12) United States Patent
Rüller et al.

(10) Patent No.: US 12,708,727 B2
(45) Date of Patent: Aug. 18, 2026

(54) DEVICE FOR SUPPORTIVE RESPIRATION OF A LIVING BEING AND COMPUTER PROGRAM

(71) Applicant: FORSCHUNGZENTRUM BORSTEL LEIBNIZ LUNGENZENTRUM, Borstel (DE)

(72) Inventors: Stephan Rüller, Bargteheide (DE); Susanne Greve, Hamburg (DE)

(73) Assignee: FORSCHUNGZENTRUM BORSTEL LEIBNIZ LUNGENZENTRUM, Borstel (DE)

( * ) Notice: Subject to any disclaimer, the term of this patent is extended or adjusted under 35 U.S.C. 154(b) by 1157 days.

(21) Appl. No.: 17/627,225

(22) PCT Filed: Jul. 22, 2020

(86) PCT No.: PCT/EP2020/070687
§ 371 (c)(1),
(2) Date: Jun. 10, 2022

(87) PCT Pub. No.: WO2021/018691
PCT Pub. Date: Feb. 4, 2021

(65) Prior Publication Data

US 2022/0305227 A1 Sep. 29, 2022

(30) Foreign Application Priority Data

Jul. 26, 2019 (DE) ........................ 10 2019 120 307

(51) Int. Cl.
*A61M 16/00* (2006.01)

(52) U.S. Cl.
CPC ... *A61M 16/024* (2017.08); *A61M 2016/0027* (2013.01); *A61M 2016/0033* (2013.01); *A61M 2230/40* (2013.01)

(58) Field of Classification Search
CPC ............ A61M 16/024; A61M 2230/40; A61M 2016/0015; A61M 16/00; A61M 2016/0027; A61B 5/082
See application file for complete search history.

(56) References Cited

U.S. PATENT DOCUMENTS 7,845,350 B1 * 12/2010 Kayyali ............ A61M 16/0051 128/204.23
2005/0109340 A1 * 5/2005 Tehrani ............... A61M 16/026 128/204.23

(Continued)

FOREIGN PATENT DOCUMENTS

CN 101043913 A 9/2007
CN 109069030 A 12/2018

(Continued)

*Primary Examiner* — Brandy S Lee
*Assistant Examiner* — Rohan Patel
(74) *Attorney, Agent, or Firm* — WCF IP

(57) ABSTRACT

The invention relates to a device (1) for supportive respiration of a living being (3), said device having a sensor arrangement, a programmable control unit (10) and an air conveyance unit (6), which is controllable by the control unit (10). The sensor arrangement has a pressure sensor (9) and an air flow sensor (11), which are designed for the temporally successive detection of respiratory pressure values and respiratory air flow values of the living being (3). The programmable control unit (10) is designed to evaluate respiratory air pressure profiles and respiratory air flow profiles formed from the temporally successive respiratory pressure values and respiratory air flow values detected by the sensor arrangement In order to provide respiration for the living being (3) which is in particular comfortable and individually adapted to the current needs of the living being (3), according to the invention the programmable control unit (10) is designed to detect unsuccessful respiratory movements of the living being (3) and the cause thereof on (Continued)

the basis of characteristic features of the respiratory pressure profiles and/or the respiratory air flow profiles. The invention furthermore relates to a computer program having program code means, designed to carry out a method for supportive respiration of a living being (3) by means of a respirator device (1) when the computer program is executed on a computer unit of the respirator device (1).

23 Claims, 7 Drawing Sheets

(56) References Cited

U.S. PATENT DOCUMENTS

2008/0110461 A1* 5/2008 Mulqueeny ....... A61M 16/0051 128/204.23
2010/0050085 A1 2/2010 Blike et al.
2012/0000470 A1 1/2012 Milne et al.
2012/0318268 A1* 12/2012 Ruller .................. A61M 16/00 128/204.23
2015/0090258 A1 4/2015 Milne et al.
2019/0015614 A1* 1/2019 Alahmadi ............. A61B 5/082
2020/0046923 A1* 2/2020 Hanafialamdari ..... G16H 20/40
2021/0205558 A1 7/2021 Vicario et al.

FOREIGN PATENT DOCUMENTS

DE 20 2005 015 676 U1 3/2006
DE 20 2005 017 045 U1 8/2006
DE 10 2005 031 808 A1 10/2006
DE 10 2005 049 643 A1 1/2007
DE 11 2007 002 265 T5 10/2009
DE 10 2017 011 610 A1 6/2018
DE 11 2017 000 410 T5 10/2018
DE 10 2018 004 341 A1 12/2019
EP 0 956 877 A1 11/1999
WO 2006/079152 A1 8/2006
WO WO-2010067236 A1 * 6/2010 ........ A61M 16/0051
WO 2019/094736 A1 5/2019

* cited by examiner

DEVICE FOR SUPPORTIVE RESPIRATION OF A LIVING BEING AND COMPUTER PROGRAM

The invention relates to a device for supportive ventilation of a living being. The invention further relates to a computer program with program code means.

Generally, the invention relates to the field of supportive ventilation of patients with breathing problems. Supportive ventilation refers here to the ventilation of living beings who perform breathing movements independently during ventilation. For example, this includes assisted ventilation and partially controlled ventilation, in which a respiratory effort on the part of the living being is detected by the device and, depending on the natural respiration of the living being, an inhalation ("inspiration") or an exhalation ("expiration") by the living being is promoted in the airways of the living being by a negative or positive pressure induced by the device relative to the actually existing pressure. An inspiration is a breathing phase with a predominantly inward flow of air into the living being, while an expiration is a breathing phase with a predominantly outward flow of air out of the living being. Furthermore, controlled ventilation is known in medicine and must be distinguished from supportive ventilation in the sense that patients under controlled ventilation do not perform independent breathing movements, or the ventilation is forced on the patient and the latter has to adapt to it through his independent respiratory efforts. In controlled ventilation, breathing frequencies and thus inspiration and expiration phases are predefined by the device, whereas in assisted ventilation these are automatically adapted by the device to the respiration independently performed by the living being. Partially controlled ventilation is based on assisted ventilation, but a minimum breathing frequency ("safety frequency" or "backup frequency") is predefined by the device. Examples of devices for supportive ventilation are BiPAP-S, Bilevel-S or PSV devices in the case of assisted ventilation, PCV or BiPAP-T devices in the case of controlled ventilation, and BiPAP-ST or aPCV devices in the case of partially controlled ventilation.

COPD patients, especially those with hypercapnic respiratory insufficiency, may be mentioned as an example of living beings requiring supportive ventilation. In these patients, structural changes have occurred in the lungs as a result of various diseases, and these changes necessitate increased work of the respiratory muscles in order to guarantee adequate gas exchange. As the disease progresses, the respiratory muscles become increasingly exhausted, as a result of which shortness of breath may be felt, even with very little exertion. In severe cases, the respiratory muscles and the respiratory drive, especially at night during sleep, are no longer able to adequately compensate for the structural changes in the lungs due to increased depth of respiration and increased breathing frequency, and ventilatory insufficiency occurs.

EP 2542286 A2 discloses a ventilator with a controllable air delivery unit or a valve control unit with a pressure-regulating valve, the ventilator having an air mass meter, a pressure sensor and a programmable control unit. In order to avoid undesired hyperdistension of the lungs of the ventilated living being, an early reduced pressure curve in the inhalation phase and a dynamically regulated counterpressure in an exhalation phase of the living being are provided by the control of the air delivery unit or valve control unit.

WO 2006/079152 A1 discloses a method and a system for detecting inefficient breathing movements of a ventilated living being. For this purpose, an expiratory air flow of the living being is monitored for disturbances.

It is the object of the invention to make available an improved device for supportive ventilation, which device provides ventilation that is particularly comfortable for the living being and that is individually adapted to the current requirements of the living being.

This object is achieved with the device according to claim 1 and with the computer program according to claim 23. Advantageous embodiments are described in the subclaims.

The device is used for supportive ventilation of a living being, for example a human. The supportive ventilation may be necessary, for example, due to disease of the airways or lungs of the living being, which is why the living being is also referred to as a patient in this application. The device has a controllable air delivery unit, which for example has a fan, a pump, a controllable turbine or an air compressor, e.g. a reciprocating compressor. To control the amount of air released, the air delivery unit can additionally have a pressure control valve or a valve arrangement. A valve control device can also be provided instead of the air delivery unit. The valve control device can be connected as an auxiliary device between a conventional ventilator and the living being to be ventilated.

The air delivery unit can for example optionally, in particular automatically, generate a continuously adjustable negative or positive pressure, for example by adapting the direction and speed of rotation of a fan. In this way, the living being can be provided with the respiratory support that is currently required in each case.

In the prior art, it is customary that generic devices for inspiration raise the ventilation pressure supplied by the device (IPAP=Inspiratory Positive Airway Pressure, ventilation pressure during inspiration) and lower it for expiration (EPAP=Expiratory Positive Airway Pressure, ventilation pressure during expiration). The IPAP and EPAP are usually determined by a therapist and set on the device. In addition to the IPAP and EPAP, there are often specifications made for the ventilation frequency, the IPAP time (time for which the inspiratory pressure is set in the inhalation phase), the ratio of the times of IPAP/EPAP, and a sensitivity for inspiration and expiration triggers explained below. Ventilation is technically considered efficient if a sufficient tidal volume and/or a sufficient minute volume is achieved. The sufficient level is set on the basis of, among other things, empirical values, the underlying ventilation indication, the disease, and blood gas analyses.

The switchover of the device from EPAP to IPAP marks the end of an expiration mode and the start of an inspiration mode, which lasts until the device switches from IPAP to EPAP. The switching of the device from IPAP to EPAP marks the end of an inspiration mode and the start of an expiration mode, which lasts until the device switches from EPAP to IPAP.

The device has a sensor arrangement with a pressure sensor and an air flow sensor. The pressure sensor can be a differential pressure sensor for example, while the air flow sensor is a pneumotachograph for example. Both sensors can be provided in a common housing or be spatially separate from each other. To detect respiratory air pressure values and respiratory air flow values of the living being, the sensors are arranged, for example, in or on a breathing mask or in or on a connecting hose between the ventilator and the breathing mask or in a valve control unit of the device. In very general terms, the words "a" or "an" in this application are not to be construed as a number, but as an indefinite article with the literal meaning of "at least one". Thus, for example, a plurality of pressure sensors or air flow sensors can be provided. The pressure sensor and the air flow sensor are designed for the temporally successive detection of respiratory air pressure values and respiratory air flow values of the living being, such that the sensors are suitable for continuous measurement of the stated values.

The detected respiratory air pressure values and respiratory air flow values are, for example, transmitted continuously or quasi-continuously to a programmable control unit of the device and evaluated by this. For this purpose, the programmable control unit has a suitable computing unit and any necessary storage means and/or suitable software in order, for example, to evaluate several temporally successive respiratory air pressure values and/or respiratory air flow values individually or in relation to one another. On account of the temporally successive respiratory air pressure values and respiratory air flow values, these are also referred to in the application documents as respiratory air pressure curves and respiratory air flow curves, in order to distinguish them from the evaluation of individual, time-independent absolute values, for example in the context of exclusive threshold value monitoring. Respiratory air pressure curves and respiratory air flow curves can in practice be graphically displayed, for example, as function curves or curve segments for illustration purposes and can thus depict a relative or absolute time curve of pressure or air flow values. During the evaluation, the absolute respiratory air pressure values and respiratory air flow values can be considered at different time points, as well as relative changes over time of the respective values. In particular, a coherent evaluation of the respiratory air pressure curves and respiratory air flow curves in relation to one another can also be provided.

According to the invention, the programmable control unit is designed to detect frustrated breathing movements of the living being associated with ventilation, on the basis of characteristic features of the respiratory air pressure curves and/or respiratory air flow curves. A frustrated breathing movement during ventilation is understood to mean a respiratory effort of the living being that does not lead to the aspirated or emitted air volume that is sought with the respiratory effort, for example it is not sufficiently detected as a respiratory effort by a device for supportive ventilation and thus does not lead to a switchover of the device from an inspiration mode to an expiration mode, or vice versa. A frustrated breathing movement of this kind can be uncomfortable for the patient and can lead to what feels like shortness of breath or shallow breathing. However, a frustrated breathing movement can also be ineffective, especially during sleep, and only lead to increased respiratory work, which counteracts the actual goal of ventilation, since ventilation for example has the purpose of minimizing the respiratory work of the patient. Frustrated breathing movements can occur during an inspiration phase and/or an expiration phase of the living being, or at a time when there is an outwardly or inwardly directed air flow, or when the pressure applied by the device is at an IPAP level or an EPAP level. Although obstructive sleep-related respiratory regulation disorders can also lead to frustrated breathing movements, they do not arise primarily during ventilation and must therefore be fundamentally differentiated.

To identify the ventilation-associated, frustrated breathing movement (hereinafter referred to simply as frustrated breathing movement), the programmable control unit analyzes the respiratory air pressure curves and/or respiratory air flow curves formed from the respiratory air pressure values and respiratory air flow values detected in succession in time by the sensor arrangement. It was found that frustrated breathing movements can already be identified on the basis of characteristic features in the curves of the detected sensor values. Accordingly, in the present case, the frustrated breathing movement is detected in particular exclusively on the basis of the respiratory air pressure curves and/or respiratory air flow curves, such that the presence of a frustrated breathing movement can already be inferred using one or two sensors, which are usually already used for other measurement purposes in such devices. Thus, in particular, no additional sensors are required to detect frustrated breathing movements, for example no measuring probes leading into the respiratory organs, as is customary for example with esophageal probes, occlusion measurements or polygraphic or polysomnographic analyses for examining and monitoring affected patients. The invention is thus based on non-invasive detection of frustrated breathing movements. At the same time, the device according to the invention has a simple structure and a simple mode of operation.

Surprisingly, despite the evaluation being limited to one or two physical variables, it is possible to make reliable statements about the occurrence of frustrated breathing movements, since the characteristic features that occur in this case in the respiratory air pressure curves and/or respiratory air flow curves are clear, verifiable and reproducible. In this case, use is made in particular of the effect that temporal value profiles have a much higher information density than instantaneous values considered individually. In particular, temporal value profiles can also be evaluated over longer periods of time using suitable storage or transmission means and, for example, can enable long-term observations of any accompanying circumstances or triggers of frustrated breathing movements. Thus, the temporal consideration of respiratory air pressure values and respiratory air flow values can provide valuable information about the current or long-term respiration-related condition of the living being. On account of the precise analysis of the breathing of the living being within the scope of the invention, it is also possible to provide customized countermeasures for the frustrated breathing movements identified on the basis of characteristic features. In particular, if necessary, differently pronounced or differently triggered frustrated breathing movements can be distinguished on the basis of characteristic features that differ from one another, as will be explained below. The distinction makes it possible to coordinate appropriate countermeasures individually to the patient's respiration and ventilation situation.

The features characteristic of frustrated breathing movements can be maxima, minima, turning points, saddle points, amplitudes, integrals and/or derivatives at predefined time points and/or time segments of the respiratory air pressure curves and/or the respiratory air flow curves. Individual local or regional features can be viewed individually or referred to as characteristic in connection with other features. For example, in an expiration phase of a respiratory air pressure curve, a local minimum with a local maximum following it within a given period of time can be used as characteristic features of a frustrated breathing movement. In a respiratory air flow curve, for example, two respiratory air flow increases following each other within a predetermined time span can be used in an expiration phase as characteristic features of a frustrated breathing movement. Oscillations occurring in the respiratory air flow curves and/or respiratory air pressure curves in predefined time spans can also be used as characteristic features of one or more consecutive frustrated breathing movements. These are examples and are not to be regarded as an exhaustive list of characteristic features, especially since the precise detection and analysis of frustrated breathing movements on the basis of the respiratory air flow and respiratory air pressure curves can be highly complex, depending on the patient's respiration and ventilation status.

According to an advantageous embodiment, the characteristic features are characteristic deviations from predefined reference respiratory air pressure curves and/or reference respiratory air flow curves. In this embodiment, for example, the programmable control unit compares the respiratory air pressure curves and/or respiratory air flow curves detected by the sensor arrangement with reference curves; for example, these are computationally or graphically superimposed, and the shape, intensity and degree of any differences between the detected curves and the reference curves are determined. For example, deviations, configured as respiratory air pressure or respiratory air flow peaks, of the currently detected respiratory air pressure curves and/or respiratory air flow curves from the reference curves at certain times, in particular during the expiration phase, can be used as characteristic deviations. The reference respiratory air pressure curves and/or reference respiratory air flow curves can be predefined, for example, as reference curves stored in advance and entered in the programmable control unit. It is also possible for the device to "learn" such reference respiratory air pressure curves and/or reference respiratory air flow curves on the basis of previous evaluations and even to store them in the programmable control unit in order to take better account of the individual breathing conditions of the patient. Such a learning process can, for example, be initiated and carried out under medical supervision in order to monitor an at least approximately ideal regular ventilation process and in order not to make it more difficult to detect frustrated breathing movements when the curves are later compared with reference curves.

According to an advantageous embodiment, the programmable control unit has a memory unit for storing predefined reference respiratory air pressure curves and/or reference respiratory air flow curves and/or reference features for characteristic features of frustrated breathing movements, in order to facilitate the internal evaluation of the deviations and/or features through comparison.

According to an advantageous embodiment, the memory unit has various disease-specific reference respiratory air pressure curves and/or reference respiratory air flow curves and/or various disease-specific reference features for characteristic features of frustrated breathing movements. In this way, features of frustrated breathing movements that are characteristic of specific diseases can be taken into account more precisely and individually. The reference respiratory air pressure curves and/or reference respiratory air flow curves and/or the reference features can, for example, be stored in tabular form in a memory unit of the programmable control unit, such that the control unit can select or limit the affected features or curves in columns or rows. According to an advantageous embodiment, the device has a setting option for selection of the specific disease or the degree of a specific disease by a person, for example a therapist or patient. The setting option can be, for example, a user interface or a data interface for storage media. Alternatively or in addition, the programmable control unit is designed for automatic detection of the current disease, for example on the basis of features of the respiratory air pressure curves and/or respiratory air flow curves that are characteristic of the respective disease.

According to an advantageous embodiment, the programmable control unit is designed to detect frustrated breathing movements of the living being on the basis of an occurring phase divergence between the actual ventilation phase of the living being and a ventilation phase carried out by the device. In this case, the device automatically or independently detects that a switchover of the device from an expiration mode to an inspiration mode or vice versa has taken place incorrectly, for example too early or too late or not at all. To detect the phase divergence, the aforementioned characteristic features of the respiratory air pressure curves and/or respiratory air flow curves can be used, for example by the programmable control unit identifying characteristic deviations from predefined reference respiratory air pressure curves and/or reference respiratory air flow curves. In an advantageous embodiment, the programmable control unit can also determine the extent of the phase divergence that occurs, for example by determining a time offset between expected characteristic features and actually established characteristic features. It is thus possible to determine the extent to which an inspiration mode or expiration mode of the device lags behind or runs ahead of the actual inspiration or expiration of the living being or is completely dissociated from it.

According to an advantageous embodiment, the programmable control unit is designed to differentiate between a frustrated breathing movement that occurs as a result of an intrinsic PEEP of the living being and a frustrated breathing movement that occurs as a result of a trigger insufficiency (which will be explained below), on the basis of characteristic features of the respiratory air pressure curves and/or respiratory air flow curves. In this way, two important and frequently occurring causes of frustrated breathing movements can be detected and distinguished by the device.

The abbreviation PEEP stands for the technical term "Positive End-Expiratory Pressure" and thus for the pressure existing in the airways of the living being at the end of the exhalation phase. In the event of incomplete exhalation, which can occur for example on account of the pressure regulated by a supportive ventilator or in particular on account of the dynamically induced counterpressure in the expiration phase, this residual pressure in the respiratory organs can increase at the end of the exhalation phase and is then referred to as intrinsic PEEP or auto PEEP. The intrinsic PEEP can be very heterogeneous locoregionally in the lungs of the living being. In particular, incomplete exhalation can also occur if the patient inhales but the exhalation has not yet ended.

In particular, over several breathing cycles, an increasing intrinsic PEEP leads to an increase in the respiratory load and forms, for the patient, a threshold that has to be overcome with each inspiration in addition to a load that is positively correlated with the depth of respiration. In addition, the increasing intrinsic PEEP leads to an increasing and also heterogeneous hyperdistension in the lungs of the living being, since the residual pressure can no longer sufficiently escape into the environment. Thus, the intrinsic PEEP is not only uncomfortable for the patient, it is also dangerous. It can lead to sensations of a shortness of breath, but also to negative effects on the cardiovascular situation. Pendelluft can also arise during ventilation. The ventilation can also become ineffective, which leads to additional stress on the lung structure. The build-up of an intrinsic PEEP should therefore be avoided or at least reduced as much as possible during supportive ventilation of a living being. It should be noted here that the intrinsic PEEP can change continuously, for example depending on the disease, the infection situation, mucus build-up, the rate of breathing or the psychological patient situation.

During supportive ventilation, an intrinsic PEEP can lead to frustrated breathing movements by the patient, in which the residual pressure in the airways can change as a result of inefficient respiratory efforts. This frustrated breathing movement can be read off from the features characteristic of the intrinsic PEEP in the respiratory air pressure curves and/or respiratory air flow curves, such that the intrinsic PEEP as a trigger of a frustrated breathing movement can be differentiated from other causes.

In the context of supportive ventilation, it is also possible that the device used for this purpose does not detect an incipient inhalation or exhalation process of the living being, or detects it at an incorrect time, due to the trigger. To identify the breathing phase, an inspiration and/or expiration trigger is usually used in such devices, which trigger detects the change in the breathing direction of the living being based on a measured pressure change or air flow change at the end of an inspiration or expiration phase and initiates the corresponding inspiration or expiration mode of the device, for example in order to generate a counterpressure, which supports the expiration by the patient, or a pressure different from the pressure present during inspiration. The sensitivity of such an inspiration and/or expiration trigger is variable and in particular adjustable in practice since, depending on the state of the living being, for example asleep or awake, the characteristic features of an incipient inspiration or expiration can be differently pronounced. An incorrect detection of the actual ventilation phase of the living being by the device, on account of too high or too low a trigger sensitivity, is referred to as trigger insufficiency. A parameter-related trigger insufficiency of this kind can occur as insufficiency of the inspiration trigger and/or as insufficiency of the expiration trigger. A setting that is too sensitive can, for example on account of a slight pressure fluctuation, lead contrary to the patient's intention to a premature initiation of the inspiration mode, whereas an overly insensitive setting leads by contrast to an expiration mode that is too late or is even skipped. A further complicating factor is that the trigger sensitivity is influenced for example by leakages in the device or the living being, for example through mouth or mask leakages or a technical leakage in the device. This can lead in particular to leakage-related trigger insufficiency of the inspiration trigger. If such leakage is present, the device automatically generates a higher counterpressure in order to compensate for the leakage, such that an inspiration trigger of the device does not identify a negative pressure possibly induced by the patient at the beginning of the inspiration. A frustrated breathing movement caused by trigger insufficiency can be read off from characteristic features in the respiratory air pressure curves and/or respiratory air flow curves, wherein parameter-related and leakage-related trigger insufficiency as triggers of a frustrated breathing movement can be differentiated from other causes (e.g. intrinsic PEEP). The device can also be designed to determine a leakage-related trigger insufficiency with the aid of measurable leakage values of the device and, for example, to compare the measured leakage values with leakage values from previous breathing cycles.

On account of the respectively different characteristic features of a frustrated breathing movement occurring as a result of an intrinsic PEEP or a trigger insufficiency, the programmable control unit is thus able to identify the respective cause of the frustrated breathing movement. Trigger insufficiency, but also an intrinsic PEEP, can lead to a phase divergence of the actual ventilation phase of the living being and the ventilation phase carried out by the device. The phase divergence can be detected by the device, for example on the basis of characteristic features in the respiratory air pressure curves and/or respiratory air flow curves.

According to an advantageous embodiment, the programmable control unit is designed to distinguish between a frustrated breathing movement occurring as a result of a leakage-related trigger insufficiency and a frustrated breathing movement occurring as a result of a parameter-related trigger insufficiency, on the basis of characteristic features of the respiratory air pressure curves and/or respiratory air flow curves. In this way, the control unit is suitable for further detection and differentiation of two possible triggers for a trigger insufficiency that occurs.

A leakage-related trigger insufficiency arises, for example, due to the above-described mask leakage or technical leakages of the device. The leakage values of the device are determined, for example, as a function of the therapy pressure and on the basis of empirical values or measurements and are incorporated as a correction value into the control calculations. In this case, inaccuracies can arise, for example on account of the assumptions made and of averaged values, and these can have an indirect effect on the sensitivity of the inspiration and expiration triggers. Such a leakage-related trigger insufficiency can be identified on the basis of characteristic features of the respiratory air pressure curves and/or respiratory air flow curves, for example within an expiration phase on the basis of a respiratory air flow increase identified as a bulge during the increase in the respiratory air flow curve and a substantially simultaneous respiratory air pressure increase identified as a bulge.

A parameter-related trigger insufficiency arises on account of an imprecise pre-setting of the trigger parameters of the programmable control unit, such that the inspiration and/or expiration trigger is set to be too sensitive or too insensitive. This is therefore a trigger insufficiency that is directly influenced by specific device settings. A parameter-related trigger insufficiency is detectable on the basis of characteristic features of the respiratory air pressure curves and/or the respiratory air flow curves, for example within an expiration phase on the basis of a respiratory air flow increase identified as a bulge during the increase in the respiratory air flow, and respiratory air pressure changes occurring during this respiratory air flow increase in the form of a respiratory air pressure reduction have the shape of a peak, and a subsequent respiratory air pressure increase having the shape of a peak in the respiratory air pressure curve during the increase in the respiratory air flow.

In view of the fact that a leakage-related trigger insufficiency and a parameter-related trigger insufficiency can be distinguished by the programmable control unit, the latter can be designed to initiate appropriate countermeasures. For example, when a leakage-related trigger insufficiency is identified, the programmable control unit can suitably adapt the above-described correction values to take account of leakage values or can also regulate them dynamically until no leakage-related trigger insufficiency can any longer be detected on the basis of characteristic features in the respiratory air flow curves and/or respiratory air pressure curves. On the other hand, when a parameter-related trigger insufficiency is identified, the programmable control unit can independently adapt the predefined parameter sets to the inspiration and/or expiration trigger in a suitable manner, request a user to change the parameter sets, or also perform dynamic control of the parameters until no parameter-related trigger insufficiency can any longer be detected on the basis of characteristic features in the respiratory air flow curves and/or respiratory air pressure curves.

According to an advantageous embodiment, the programmable control unit is designed to detect a frustrated breathing movement on the basis of the time point, the time span and/or the form of a respiratory air pressure and/or respiratory air flow increase or reduction in the respiratory air pressure curves and/or respiratory air flow curves. For example, a time point of the respiratory air pressure and/or respiratory air flow increase or reduction in an expiration phase, in the first or second half of the expiration phase or during the transition from an inspiration phase to an expiration phase can be used as a characteristic feature of a frustrated breathing movement. Experience has shown here that features characteristic of frustrated breathing movements occur increasingly in expiratory sections of the respiratory air pressure curves and/or respiratory air flow curves. A duration of the respiratory air pressure and/or respiratory air flow increase or reduction, which can typically be 0.1 to 1.0 second, can also be used as a characteristic feature of a frustrated breathing movement. As regards the form, the respiratory air pressure and/or respiratory air flow increase or reduction can be shaped, for example, as a bulge or peak. A bulge represents an arc-shaped increase or decrease; in the case of a peak, the increase or decrease has a kink, in particular a kink with an acute angle between the curve rising before the maximum and falling after the maximum. During the evaluation, several of the aforementioned criteria can also be placed in relation to each other. For example, if a bulge-shaped respiratory air pressure and/or respiratory air flow increase or reduction occurs in the middle of the expiration phase detected by the device for 0.2 to 0.7 second, it is possible to infer the presence of a frustrated breathing movement. The maxima, minima, turning points, saddle points, amplitudes, integrals and/or derivatives at predefined time points and/or time segments of the respiratory air pressure curves and/or respiratory air flow curves can be used as it were to identify and differentiate the aforementioned curves.

The device is in particular designed to distinguish between a frustrated breathing movement occurring as a result of an intrinsic PEEP of the living being and a frustrated breathing movement occurring as a result of a trigger insufficiency, on the basis of the time point, the time span and/or the form of a respiratory air pressure and/or respiratory air flow increase or reduction in the respiratory air pressure curves and/or respiratory air flow curves. This differentiation is based on the knowledge that the characteristic features of frustrated breathing movements as a result of an intrinsic PEEP or of a trigger insufficiency differ from one another, particularly with respect to the time points, time spans and/or the forms of respiratory air pressure and respiratory air flow increases or reductions.

According to an advantageous embodiment, the programmable control unit is designed to detect a frustrated breathing movement on the basis of characteristic features of the respiratory air flow curves and related characteristic features of the respiratory air pressure curves. This improves the detection accuracy. For example, the control unit first determines a respiratory air flow increase in the respiratory air flow curve and then checks whether there is a respiratory air pressure increase in the respiratory air pressure curve in a predefined time span before, after or at the same time as the respiratory air flow increase. In addition to the time point, the time spans and forms of respiratory air pressure and respiratory air flow increases can also be related to one another. The detection can thus take place in the sense of a multi-factor dependency on the basis of characteristic features of the respiratory air flow curves and respiratory air pressure curves in combination.

The programmable control unit is designed in particular to distinguish between a frustrated breathing movement occurring as a result of an intrinsic PEEP of the living being and a frustrated breathing movement occurring as a result of a trigger insufficiency, on the basis of characteristic features of the respiratory air flow curves and related characteristic features of the respiratory air pressure curves. This improves the accuracy of the distinction. For example, the control unit first determines a bulge-shaped respiratory air flow increase in the respiratory air flow curve and then checks whether there is a bulge-shaped respiratory air pressure increase at substantially the same time and during substantially the same time span. If this is the case, the control unit detects a frustrated breathing movement as a result of a leakage-related trigger insufficiency. In particular, the simultaneously occurring increases in the respiratory air flow and respiratory air pressure curves can have substantially the same form, for example the same gradients at the same time points or a substantially identical integral over the time of the respective increase.

Furthermore, the control unit can also first determine a bulge-shaped respiratory air flow increase in the respiratory air flow curve and then check whether there is a peak-shaped respiratory air pressure increase in a predefined time span, for example before the end time or during a second half of the time of the respiratory air flow increase. If this is the case, the control unit detects a frustrated breathing movement as a result of an intrinsic PEEP. In particular, the peak in the respiratory air pressure curve can be smaller in comparison to the bulge in the respiratory air flow curve, for example having a smaller integral over the time of the increase.

In a further characteristic combination of features of a frustrated breathing movement as a result of a trigger insufficiency, there is a bulge-shaped respiratory air flow increase in the respiratory air flow curve, whereas in the same time span of the respiratory air flow increase there is initially a peak-shaped respiratory air pressure reduction and then a peak-shaped respiratory air pressure increase. If this is the case, the control unit detects a frustrated breathing movement as a result of a parameter-related trigger insufficiency. In particular, the peaks in the respiratory air pressure can each be smaller compared to the bulge in the respiratory air flow curve, for example having a smaller integral over the time of the increase.

The programmable control unit is designed to identify the characteristic features and to evaluate them as a function of one another in order to detect a frustrated breathing movement and, as regards the cause of the latter, to differentiate between intrinsic PEEP and trigger insufficiency.

According to an advantageous embodiment, the programmable control unit is also designed to perform oscillometric airway resistance measurements. Performing oscillometric airway resistance measurements can facilitate the detection of an intrinsic PEEP of the living being, such that a better distinction is possible between a frustrated breathing movement occurring as a result of an intrinsic PEEP of the living being and a frustrated breathing movement occurring as a result of a trigger insufficiency. The oscillometric airway resistance measurement can be implemented, without additional device components, by suitably activating the air delivery unit. In oscillometric airway resistance measurements, which are known for example in the form of so-called impulse oscillometry (IOS) or forced oscillation technology (FOT), the ventilation pressure generated by the device is superposed with low-amplitude, high-frequency pressure pulses. The flow resistance and thus the airway resistance can be determined on the basis of the measured ratio of the pressure difference to the respiratory flow. An intrinsic PEEP of the living being can be inferred indirectly or directly from the airway resistance. Thus, the detection accuracy and distinction accuracy of the device for frustrated breathing movements that occur as a result of intrinsic PEEP or trigger insufficiency is increased.

According to an advantageous embodiment, the programmable control unit is designed to determine the frequency and/or intensity of the intrinsic PEEP, or of the trigger insufficiency as a result of which the frustrated breathing movement occurs. For this purpose, for example, the time extent, the amplitude, the gradient, the integral and the number of respiratory air pressure and/or respiratory air flow increases or reductions are determined and evaluated by the control unit, and for example compared with reference values or threshold values. The analysis can in particular also take place over several breathing cycles, for example in order to differentiate recurring symptoms from irregularities that occur just once, or in order to observe an increase or decrease in the symptoms.

Here, according to an advantageous embodiment, the programmable control unit is designed to output a for example optical, acoustic and/or haptic alarm signal when a predefined threshold value for the frequency and/or intensity of the intrinsic PEEP or trigger insufficiency is exceeded, for example in order to indicate when a health-critical state is reached and to enable the living being or other persons present to initiate an appropriate response, for example an emergency call.

According to an advantageous embodiment, the programmable control unit is designed to automatically vary control parameters of the air delivery unit when a frustrated breathing movement is detected. Thus, the device itself can already initiate suitable countermeasures in order to reduce or avoid further frustrated breathing movements.

According to an advantageous embodiment, the programmable control unit is designed for continuous regulating automatic variation of control parameters of the air delivery unit in order to reduce and/or eliminate the features of the respiratory air pressure curves and/or respiratory air flow curves that are characteristic of the frustrated breathing movement. In this case, the device itself iteratively approaches the air flow parameters most favorable for the patient by continuously changing the control parameters in the sense of a control loop. For example, in one expiration phase, or consecutively in several expiration phases, the dynamic counterpressure generated by the air delivery unit is increased or decreased incrementally or intermittently for a period of time that is shorter than an expiration phase, until the programmable control system detects, on the basis of characteristic features of the respiratory air pressure curves and/or respiratory air flow curves, the occurrence of a frustrated breathing movement. When the frustrated breathing movement is identified, the induced air pressure is then slightly reduced again or increased, or the intermittent air pressure increase is started later, and a check is made as to whether further frustrated breathing movements occur. This process can be repeated at any desired frequency in order to determine at each time suitable control parameters which reduce or avoid the occurrence of frustrated breathing movements. In this way, it is possible, for example, that a physician or therapist only sets a value range on the device for the IPAP and EPAP and, if necessary, a backup frequency for the respiration, and the IPAP and/or EPAP value currently most favorable for avoiding frustrated breathing movements, and further parameters too, are determined and set by the device itself on the basis of the respiratory air flow curves and respiratory air pressure curves. A backup frequency can be a minimum respiration frequency that ensures a sufficient number of breaths by the living being.

A continuous, regulating automatic variation of the control parameters, which has the regulation goal of eliminating frustrated breathing movements, in particular those due to intrinsic PEEP or trigger insufficiency, is based on a fundamentally different approach than is customary in current ventilation concepts. Thus, current guidelines on non-invasive ventilation are primarily based on pCO2 values as a control criterion, with high pressure amplitudes in particular being intended to promote the CO2 exchange of the patient. By contrast, according to the embodiment described above, the pressure values for example, in particular the IPAP, should be regulated only such that no more frustrated breathing movements occur, since regulated supportive ventilation of this kind increases the wellbeing of the living being, and harmful effects of too great a pressure on the lungs are avoided.

The programmable control unit can be designed to automatically vary control parameters of the air delivery unit in order to reduce the features of the respiratory air pressure curves and/or respiratory air flow curves that are characteristic of the frustrated breathing movement, according to a predefined intrinsic minimum PEEP. It is in this way possible, for certain applications and living beings, for example for patients with a considerably increased pCO2 value, to set a certain permissible intrinsic basic or minimum PEEP (minimum PEEP), which is not fallen below during the automatic variation of control parameters of the air delivery unit for reducing the features of the respiratory air pressure curves and/or respiratory air flow curves that are characteristic of the frustrated breathing movement.

The programmable control unit can be designed to determine a predefined intrinsic minimum PEEP on the basis of pCO2 measurements. Here, "pCO2" denotes the carbon dioxide partial pressure, which reflects the amount of carbon dioxide dissolved in the blood of the living being. For example, on the basis of measured pCO2 values or pCO2 value ranges and of information or calculation instructions stored in the control unit, the control unit can determine an intrinsic minimum PEEP and automatically vary control parameters in such a way that the intrinsic minimum PEEP is not fallen below. For checking this condition and for regulating, the control unit can be designed to use the measured pCO2 values and/or the features of the respiratory air pressure curves and/or respiratory air flow curves that are characteristic of the frustrated breathing movement. The control unit can be designed for continuous pCO2 measurement. The device can have at least one pCO2 sensor for determination, in particular for continuous determination, of pCO2 values of the living being. The pCO2 sensor can be designed for transcutaneous or end-tidal measurement of pCO2 values.

The control parameter can also be, for example, an inspiration trigger or expiration trigger for changing the device from an inspiration mode to an expiration mode, or vice versa. Thus, for example, when a frustrated breathing movement resulting from a trigger insufficiency is detected, the programmable control unit can automatically increase or reduce the sensitivity of the inspiration trigger or expiration trigger. For example, the sensitivity of the inspiration trigger or expiration trigger is increased or reduced until the programmable control unit no longer detects any frustrated breathing movement resulting from trigger insufficiency.

The change in the sensitivity of the inspiration or expiration trigger can also take place as a response to a frustrated breathing movement resulting from an intrinsic PEEP. In devices for supportive ventilation, the ratio of the current respiratory flow to the maximum respiratory flow is often used as a switchover criterion. If an intrinsic PEEP occurs, the ratio can be increased such that there is a quicker switchover from inspiration to expiration. This reduces the intrinsic PEEP. The ratio can then be reset to the original value or also reduced until characteristic features for an intrinsic PEEP are detectable again.

The control parameter can also be a respiratory air pressure and/or respiratory air flow curve, predefined by the programmable control unit, of the air delivered by the air delivery unit. For example, the air flow provided by the air delivery unit can be reduced or increased in order to suitably support the respiratory efforts of the living being. The control unit can also set different, respectively suitable respiratory air pressure and/or respiratory increases or decreases per unit of time or different minimum and maximum values of respiratory air pressure and respiratory air flow.

The control parameter can also be an air pressure and/or air flow curve of the air delivered by the air delivery unit, predefined by the programmable control unit. For example, the air flow provided by the air delivery unit can be reduced or increased in order to suitably support the respiratory efforts of the living being. The control unit can also set different, respectively suitable air pressure and/or air flow increases or decreases per unit of time or different minimum and maximum values of air pressure and air flow.

Further control parameters can also be, for example, an inspiration time or expiration time predefined by the programmable control unit, in particular a respective minimum or maximum inspiration time or expiration time, an IPAP value, an EPAP value, a pressure rise time (time in which the IPAP is reached after triggering of the inspiration) and a pressure drop time (time in which the EPAP is reached after triggering of the expiration). The control parameters mentioned are particularly suitable for reducing or avoiding a frustrated breathing movement that occurs as a result of an intrinsic PEEP. Indirect parameters, for example a predefined tidal volume, which can be influenced by the parameters described above, can also be included as control or regulation variables.

According to an advantageous embodiment, the programmable control unit can be designed to automatically reduce the backup frequency and/or the IPAP value and/or the maximum inspiration time and/or to automatically increase the expiration trigger sensitivity upon detection of a frustrated breathing movement that occurs as a result of an intrinsic PEEP of the living being. Alternatively or in addition, the programmable control unit can be designed to automatically increase the backup frequency and/or the IPAP value and/or the maximum inspiration time and/or to automatically reduce the expiration trigger sensitivity after elimination of a frustrated breathing movement that occurs as a result of an intrinsic PEEP of the living being. It is also advantageous if the programmable control unit is designed to automatically increase the backup frequency and/or the IPAP value and/or the maximum inspiration time and/or to automatically reduce the expiration trigger sensitivity upon detection of a frustrated breathing movement that occurs as a result of an intrinsic PEEP of the living being. In this way, on the basis of the four parameters mentioned, the control unit automatically sets an always optimal operating point of the device with a high level of user comfort.

A respiratory air pressure curve and/or respiratory air flow curve predefined by the programmable control unit is particularly relevant for ventilation devices with a deflation function. An air pressure and/or air flow curve predefined by the programmable control unit is particularly relevant for ventilation devices with a deflation function. Such ventilation devices generate a counterpressure when the patient exhales. Due to the breathing resistance that is provided, the air pressure or respiratory air pressure in the airways of the living being is increased in an intermittent manner and a collapse of the airways is prevented. For example, the expiration phase of the living being can be supported if, in the exhalation phase, the air pressure or respiratory air pressure in the respiratory organ is regulated, in accordance with the respiratory air flow or with exhalation parameters derived therefrom, in such a way that the respiratory air flow flowing out of the living being reaches a predetermined level. Therefore, in contrast to known ventilators, a predefined pressure is not set, and instead the air pressure or respiratory air pressure is regulated dynamically in accordance with the respiratory air flow of the exhalation, such that as a result a defined exhalation air flow can be ensured. Here, the air pressure or respiratory air pressure can be increased or reduced as required, and, by regulating the air pressure or respiratory air pressure according to the respiratory air flow, a corresponding minimum pressure in the respiratory organs can be maintained dynamically as a changing counterpressure, such that the small airways and their branches to the alveoli are kept open. A certain dynamic resistance during exhalation is thus created, which is surprisingly found by patients to be pleasant and supportive. The result of this is improved exhalation and an avoidance of the undesired hyperdistension of the lungs. In particular, just a relatively short pressure pulse during exhalation helps to open the airways. The counterpressure involves in particular an application of air pressure by the device, which air pressure increases at least in parts during the expiration phase and then falls again and is directed counter to the respiratory flow of the living being.

However, the resistance generated by the device with the deflation function can also lead to the abovementioned intrinsic PEEP if air cannot sufficiently escape from the airways and the lungs of the living being on account of the counterpressure provided by the ventilator. It is therefore important, especially for ventilation devices with an integrated deflation function, to identify the occurrence of frustrated breathing movements and, as a reaction, for example to vary the set counterpressure parameters, such as counterpressure wait time or counterpressure amplitude or, for example, also to activate or deactivate dynamic counterpressure control. Thus, according to an advantageous embodiment of the invention, a control parameter is a counterpressure and/or counterpressure curve predefined by the programmable control unit and/or a counterpressure amplitude and/or counterpressure wait time predefined by the programmable control unit during the expiration phase. The counterpressure wait time is a delay in the buildup of counterpressure after the change from an inspiration phase to an expiration phase; it is, for example, between 0 and 0.8 second after the start of expiration. According to an advantageous embodiment, the counterpressure amplitude and/or the counterpressure wait time during the expiration phase can be set as a function of each other and/or as a function of an IPAP value or IPAP value range and/or a differential pressure from IPAP to EPAP. The counterpressure wait time can be longer the higher the IPAP value or the higher the permissible IPAP value range chosen. The counterpressure amplitude, i.e. the maximum counterpressure value, can be varied depending on the existing respiratory air pressure and the counterpressure wait time. The counterpressure amplitude can be greater the higher the IPAP value or the higher the permissible IPAP value range that is chosen. The correlations between counterpressure wait time, counterpressure amplitude and IPAP value can in particular be stored in the programmable control unit. In this way, the programmable control unit can be designed to automatically determine and set an optimal counterpressure wait time and an optimal counterpressure amplitude on the basis of an IPAP value that is set by external input. Here, the control unit preferably selects a longer counterpressure wait time and a higher counterpressure amplitude the higher the input or regulated IPAP value. The counterpressure curve over time can also be varied such that, for example, a maximum counterpressure is reached or brought about sooner or later. Usually, a higher counterpressure leads to a longer expiration time. However, too high a counterpressure can make expiration more difficult, such that the counterpressure parameters are advantageously regulated as a function of the occurrence of frustrated breathing movements.

In practice, it cannot be ruled out that an intrinsic PEEP and a trigger insufficiency can occur at the same time and influence or reinforce each other. For example, the sensitivity of the inspiration trigger to an increased intrinsic PEEP can be too weak, since the residual pressure in the airways superposes a negative pressure built up by the living being for inspiration. Furthermore, strongly pronounced breathing movements, leakages and/or a simultaneous intrinsic PEEP can superpose one another and make it difficult to detect frustrated breathing movements on the basis of characteristic features in the respiratory air flow curves and respiratory air pressure curves. To reduce the aforementioned symptoms, it may be effective in such a case to take the precaution of initiating several countermeasures in combination, for example lowering the IPAP, shortening the counterpressure wait time and reducing the counterpressure. By this means, the leakages and the intrinsic PEEP are reduced at the same time. Alternatively or in addition, the above-described performance of oscillometric airway resistance measurements can be advantageous in distinguishing between intrinsic PEEP and trigger insufficiency.

According to an advantageous embodiment, the programmable control unit can furthermore be designed to detect inspiratory inhibitions of the living being on the basis of characteristic features of the respiratory air pressure curves and/or respiratory air flow curves. Compared to a frustrated breathing movement, there is no phase divergence in the case of inspiratory inhibition, but rather a reduced or even interrupted respiratory air flow of the living being during inhalation. Inspiratory inhibitions can occur through reflexes, for example through a sensitive protective reflex such as the Hering-Breuer reflex. Characteristic features of such inspiratory inhibition can be expressed in detected respiratory air pressure curves and/or respiratory air flow curves, for example as a respiratory air flow curve which drops steeply in the early inspiration phase while the IPAP level remains unchanged. In response to a detected inspiratory inhibition, the programmable control unit can be designed to automatically vary control parameters of the air delivery unit and, for example, to suitably adapt predefined respiratory air pressure curves and/or respiratory air flow curves of the air delivered by the air delivery unit, in particular also a pressure rise time, until the characteristic features of the inspiratory inhibition no longer occur. Alternatively or at the same time, the IPAP can also be reduced. Alternatively or in addition, the device can also output an optical, acoustic and/or haptic warning signal to indicate the inspiratory inhibition.

The characteristic features of the respiratory air pressure curves and/or respiratory air flow curves can also be regarded as characteristic patterns, especially if they are considered or evaluated in connection with one another, since they can repeatedly occur to the same or similar extents in frustrated breathing movements. According to an advantageous embodiment, the programmable control unit has a pattern recognition unit for recognizing characteristic features of the respiratory air pressure curves and/or respiratory air flow curves. For example, the programmable control unit can be equipped with a corresponding pattern recognition and/or classification software that can carry out computational pattern recognition and classification processes for example by means of main component analyses, discriminance analyses or support vector machines. The use of artificial neural networks is also advantageous.

Analogous to the device according to the invention for supportive ventilation of a living being, the invention also comprises a method for supportive ventilation of a living being using a ventilator, wherein, by means of a pressure sensor and an air flow sensor of the ventilator, respiratory air pressure values and respiratory air flow values of the living being that follow one another in time are recorded and, with a programmable control unit of the ventilator, respiratory air pressure curves and respiratory air flow curves formed from the respiratory air pressure values and respiratory air flow values are evaluated, and wherein frustrated breathing movements of the living being are detected on the basis of characteristic features of the respiratory air pressure curves and/or respiratory air flow curves. The advantages explained above can also be realized in this way. The ventilator can be designed as a device of the type explained above.

The characteristic features can be maxima, minima, turning points, saddle points, amplitudes, integrals and/or derivatives at predefined time points and/or time segments of the respiratory air pressure curves and/or respiratory air flow curves. The characteristic features can also be characteristic deviations from predefined reference respiratory air pressure curves and/or reference respiratory air flow curves.

The method can include storing predefined reference respiratory air pressure curves and/or reference respiratory air flow curves and/or reference features for characteristic features of frustrated breathing movements in a memory unit of the programmable control unit. In particular, it is possible to store various disease-specific reference respiratory air pressure curves and/or reference respiratory air flow curves and/or various disease-specific reference features for characteristic features of frustrated breathing movements in the storage unit.

The method can include a detection of frustrated breathing movements of the living being on the basis of a phase divergence that occurs between the actual ventilation phase of the living being and a ventilation phase carried out by the ventilator.

The method can include distinguishing between a frustrated breathing movement occurring as a result of an intrinsic PEEP of the living being and a frustrated breathing movement occurring as a result of a trigger insufficiency, on the basis of characteristic features of the respiratory air pressure curves and/or respiratory air flow curves.

The method can include distinguishing between a frustrated breathing movement occurring as a result of a leakage-related trigger insufficiency and a frustrated breathing movement occurring as a result of a parameter-related trigger insufficiency, on the basis of characteristic features of the respiratory air pressure curves and/or respiratory air flow curves.

The method can include identifying a frustrated breathing movement on the basis of the time point, the time span and/or the form of a respiratory air pressure and/or respiratory air flow increase or reduction in the respiratory air pressure curves and/or respiratory air flow curves, and in particular distinguishing between a frustrated breathing movement occurring as a result of an intrinsic PEEP of the living being and a frustrated breathing movement occurring as a result of a trigger insufficiency, on the basis of the time point, the time span and/or the form of a respiratory air pressure and/or respiratory air flow increase or reduction in the respiratory air pressure curves and/or respiratory air flow curves.

The method can include detecting a frustrated breathing movement and in particular distinguishing between a frustrated breathing movement occurring as a result of an intrinsic PEEP of the living being and a frustrated breathing movement occurring as a result of a trigger insufficiency, on the basis of characteristic features of the respiratory air flow curves and related characteristic features of the respiratory air pressure curves.

The method can further include performing oscillometric airway resistance measurements.

The method can include determining the frequency and/or intensity of the intrinsic PEEP or of the trigger insufficiency. In this case, an in particular acoustic, optical and/or haptic alarm signal can be output when a predefined threshold value for the frequency and/or intensity of the intrinsic PEEP or of the trigger insufficiency is exceeded.

The method can include an automatic variation of control parameters of the air delivery unit when a frustrated breathing movement is detected. In particular, a continuous regulating automatic variation of control parameters of the air delivery unit can be provided in order to reduce and/or eliminate the features of the respiratory air pressure curves and/or respiratory air flow curves that are characteristic of the frustrated breathing movement.

The method can include an automatic variation of control parameters of the air delivery unit in order to reduce the features of the respiratory air pressure curves and/or respiratory air flow curves that are characteristic of the frustrated breathing movement according to a predefined intrinsic minimum PEEP. Here, a predefined intrinsic minimum PEEP can be determined on the basis of pCO2 measurements.

A suitable control parameter is, for example, an inspiration trigger or expiration trigger for changing the device from an inspiration mode to an expiration mode, or vice versa. Another suitable control parameter is, for example, a respiratory air pressure curve and/or respiratory air flow curve of the air delivered by the air delivery unit, which curve is predefined by the programmable control unit. Another suitable control parameter is, for example, an air pressure curve and/or air flow curve of the air delivered by the air delivery unit, which curve is predefined by the programmable control unit. The control parameter can also be a counterpressure and/or counterpressure curve predefined by the programmable control unit and/or a counterpressure amplitude and/or counterpressure wait time predefined by the programmable control unit during the expiration phase. The counterpressure amplitude and/or the counterpressure wait time during the expiration phase can be set as a function of each other and/or as a function of an IPAP value or IPAP value range and/or as a function of a differential pressure from IPAP to EPAP.

The method can include automatically reducing the IPAP value and/or the maximum inspiration time and/or automatically increasing the expiration trigger sensitivity upon detection of a frustrated breathing movement occurring as a result of an intrinsic PEEP of the living being. Alternatively or in addition, the method can include automatically increasing the IPAP value and/or the maximum inspiration time and/or automatically reducing the expiration trigger sensitivity after elimination of a frustrated breathing movement that occurs as a result of an intrinsic PEEP of the living being.

The method can include detecting inspiratory inhibitions of the living being on the basis of characteristic features of the respiratory air pressure curves and/or respiratory air flow curves.

The method can include a pattern recognition for recognizing characteristic features of the respiratory air pressure curves and/or respiratory air flow curves.

The object of the invention is also achieved by a computer program with program code means, designed to carry out a method for supportive ventilation of a living being with a ventilator, when the computer program is executed on a computing unit of the ventilator, wherein a pressure sensor and an air flow sensor of the ventilator detect temporally successive respiratory air pressure values and respiratory air flow values of the living being and a programmable control unit of the ventilator evaluates respiratory air pressure curves and respiratory air flow curves formed from the respiratory air pressure values and respiratory air flow values, and wherein frustrated breathing movements of the living being are detected on the basis of characteristic features of the respiratory air pressure curves and/or respiratory air flow curves and in particular are differentiated with respect to their cause, for example as a result of an intrinsic PEEP of the living being or as a result of a trigger insufficiency. The advantages explained above can also be realized in this way.

The invention is explained in more detail below on the basis of an exemplary embodiment and with reference to the accompanying schematic drawings, in which.

Figure 1:
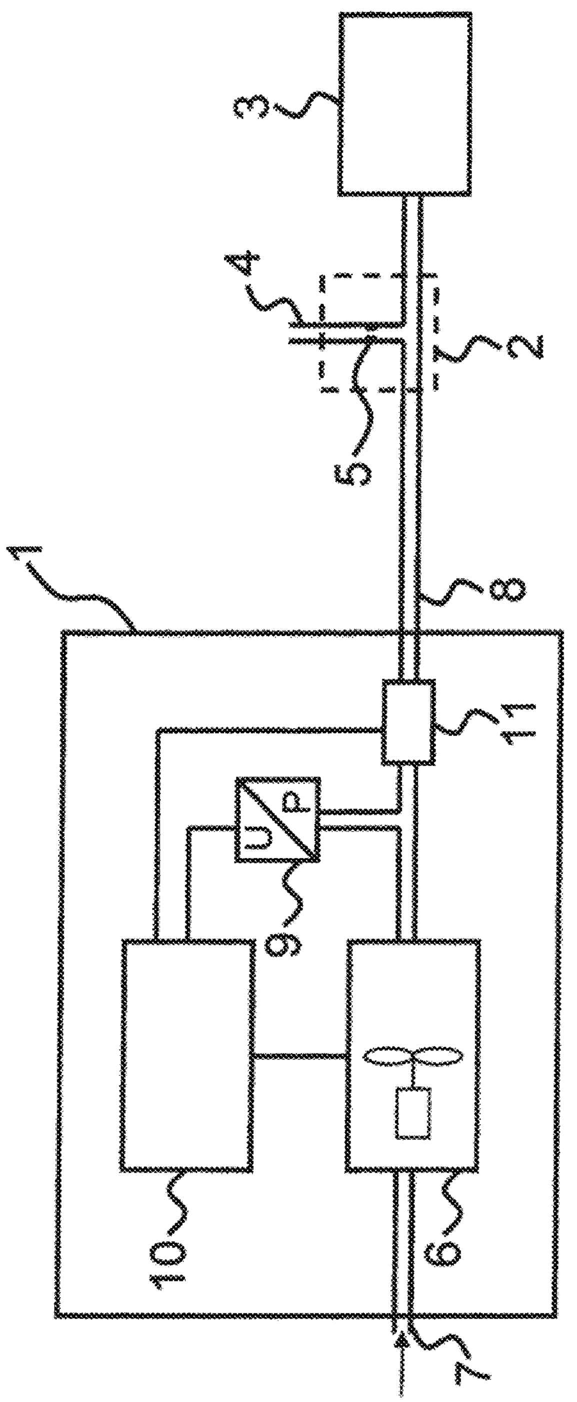
FIG. 1 shows a device for supportive ventilation of a living being.

FIG. 1 shows a device 1 for supportive ventilation of a living being 3. The device 1 has a hose 8 and a breathing mask 2 or another suitable interface for connecting the device 1 to the living being 3. The breathing mask 2 is for this purpose attachable, for example, to the mouth and/or nose or to deeper airways of the living being 3. The breathing mask 2 has an outlet 4 which is open to the atmosphere and which is connected to the hose 8 via a throttle site 5. In this way, a defined leakage can be provided in the breathing mask 2.

The device 1 has a controllable air delivery unit 6 with a fan for generating the overpressure, required for the supportive ventilation, in the respiratory organs of the living being 3. For example, via the air delivery unit 6, air is sucked in from an air inlet 7 connected to the atmosphere and, suitably compressed via the hose 8, is delivered to the breathing mask 2 and thus to the living being 3.

The device 1 has a sensor arrangement with a pressure sensor 9 and an air flow sensor 11, which are designed for temporally successive detection of respiratory air pressure values and respiratory air flow values of the living being 3. Alternatively or in addition, the air delivery unit 6 can have an integrated pneumotachographic measuring arrangement for measurement of pressure and/or volumetric flow.

The pressure sensor 9, the air flow sensor 11 and the air delivery unit 6 are connected to a programmable control unit 10 via electrical lines. The programmable control unit 10 evaluates the respiratory air pressure curves and respiratory air flow curves formed from the respiratory air pressure values and respiratory air flow values that are detected over time by the pressure sensor 9 and the air flow sensor 11. The programmable control unit 10 is designed to detect frustrated breathing movements of the living being 3 on the basis of characteristic features of the respiratory air pressure curves and/or respiratory air flow curves. The programmable control unit is moreover designed to establish the cause(s) of the frustrated breathing movements and, if necessary, to take countermeasures to reduce or avoid the frustrated breathing movements. For this purpose, it can optionally have a suitable memory unit, suitable software, transmission means and/or a pattern recognition unit (in each case not shown in any more detail).

Figure 2:
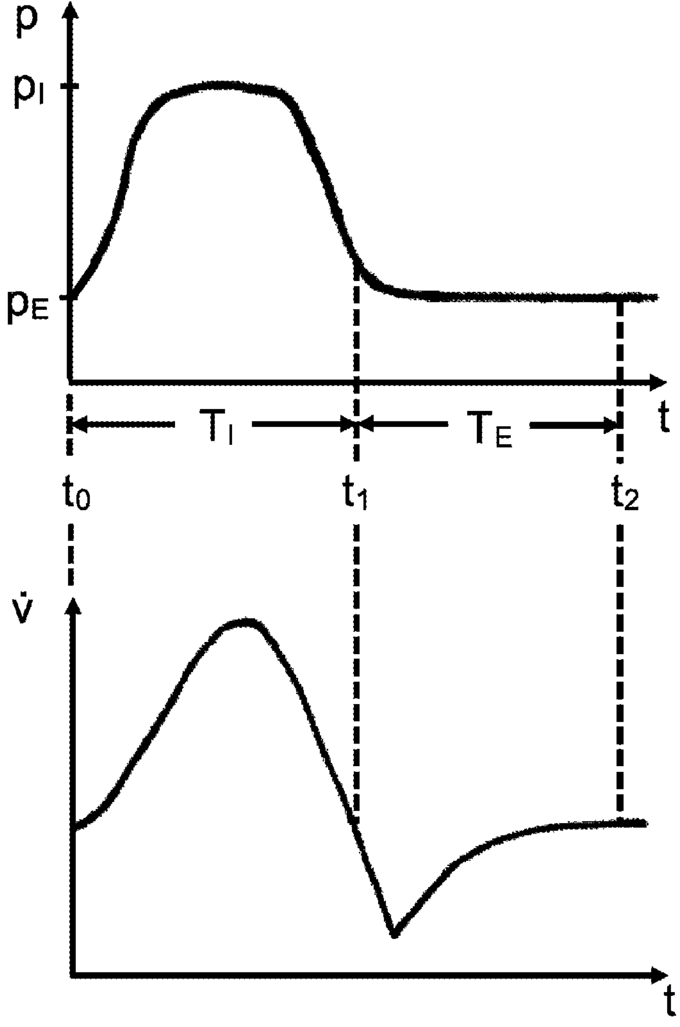
FIG. 2 shows a normal respiratory air pressure curve and respiratory air flow curve.
Figure 2:
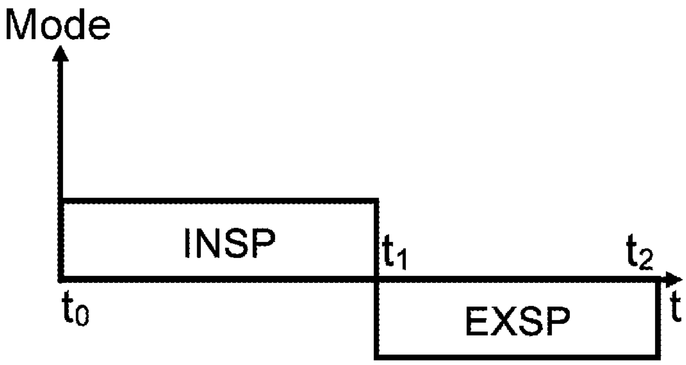

FIG. 2 shows, in a highly schematic manner, a normal respiratory air pressure curve and respiratory air flow curve, as can ideally be measured in a healthy living being under ventilation. The upper diagram shows a respiratory air pressure curve as a function of the pressure p over the time t. The middle diagram shows a respiratory air flow curve as a function of the volumetric flow v over the time t. The lower diagram shows the time sequence of ventilation modes of the device 1, here an inspiration mode INSP and an expiration mode EXSP, during a breathing cycle as a result of an automatic detection of the ventilation phase $T_I$, $T_E$ of the living being 3 by the device 1. All that is shown is one complete breathing cycle with an inspiration phase $T_I$ and an expiration phase $T_E$, which breathing cycle can be seen as representative of preceding and subsequent breathing cycles. The breathing cycle begins at the time point $t_0$ and ends at the time point $t_2$. The change from an inspiration phase $T_I$ to an expiration phase $T_E$ takes place after approximately half of the breathing cycle at the time point $t_1$. However, the time point $t_1$ can also lie considerably closer to $t_0$, such that the ratio of $T_I$ to $T_E$ can also assume values of 1:2 to 1:4 or can be even smaller. In individual cases, the time point $t_1$ can also lie closer to $t_2$. It can be seen in FIG. 2 that the respiratory air pressure in the inspiration phase $T_I$ is initially steadily increased to the IPAP value $p_I$, then assumes an approximately constant pressure level at the IPAP value $p_I$ over a certain time span and, still in the inspiration phase $T_I$, steadily decreases. By contrast, in the expiration phase $T_E$, there is no longer a build-up of pressure, but instead a constant pressure at the basal pressure level of the breathing cycle, in the present case at the level of the EPAP value $P_E$. It can also be seen in FIG. 2 that the respiratory air flow initially increases steadily in the inspiration phase $T_I$ and, after reaching a local maximum, decreases steadily still in the inspiration phase $T_I$. At the end of the inspiration phase $T_I$ or at the beginning of the expiration phase $T_E$, i.e. approximately at the time point $t_1$, the respiratory air flow changes to a value range below the initial level of the inhalation air flow, which illustrates the change in the direction of the respiratory flow of the living being. After a local minimum is reached, the respiratory air flow increases again until it has reached its initial value at the beginning of the breathing cycle and moves on to the next breathing cycle. For example, an inspiration trigger of the device 1 detects the end of an expiration $T_E$ and/or the beginning of an inspiration $T_I$ of the living being 3, idealized here at the time point $t_0$, and causes the programmable control unit 10 to switch on an inspiration mode INSP of the control unit 10. In the inspiration mode INSP, for example, the air delivery unit 6 can generate an overpressure, supporting the inspiration by the living being 3, with a predefined pressure curve. For example, an expiration trigger of the device 1 detects the end of an inspiration $T_I$ and/or the beginning of an expiration $T_E$ of the living being 3, idealized here at the time point $t_1$, and causes the programmable control unit 10 to switch on an expiration mode EXSP of the control unit 10. In the expiration mode EXSP, for example, the air delivery unit 6 can generate an overpressure, supporting the expiration by the living being 3, with a predefined pressure curve. Ideally at the time point $t_2$, the control unit 10 ends the expiration mode EXSP, for example on account of a signal from the inspiration trigger. The idealized representation of the change-over times between the two modes does not take account of any technically related delay times, for example electronic switching times. The beginning or the end of the inspiration mode INSP or expiration mode EXSP are not rigidly predefined by the control unit 10, but are dynamically adapted to the ventilation phases $T_I$, $T_E$ of the living being 3 by the detection of a corresponding respiratory effort of the living being 3.

Figure 3:
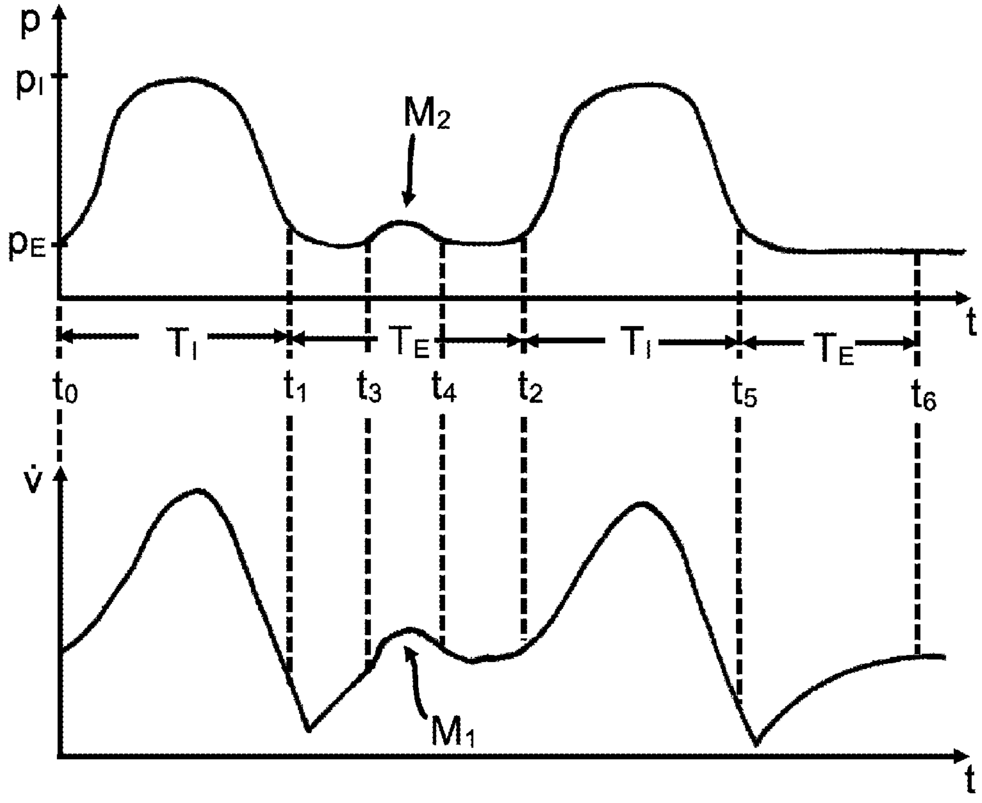
FIGS. 3-5 show respiratory air pressure curves and respiratory air flow curves over time during a breathing cycle with detectable frustrated breathing movements and during a breathing cycle without detectable frustrated breathing movements.
Figure 3:
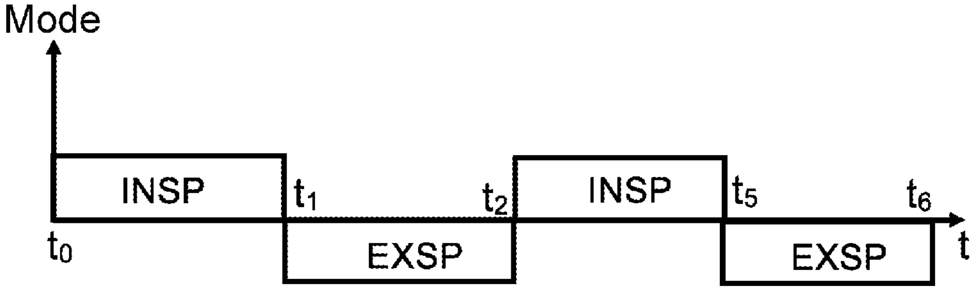
Figure 4:
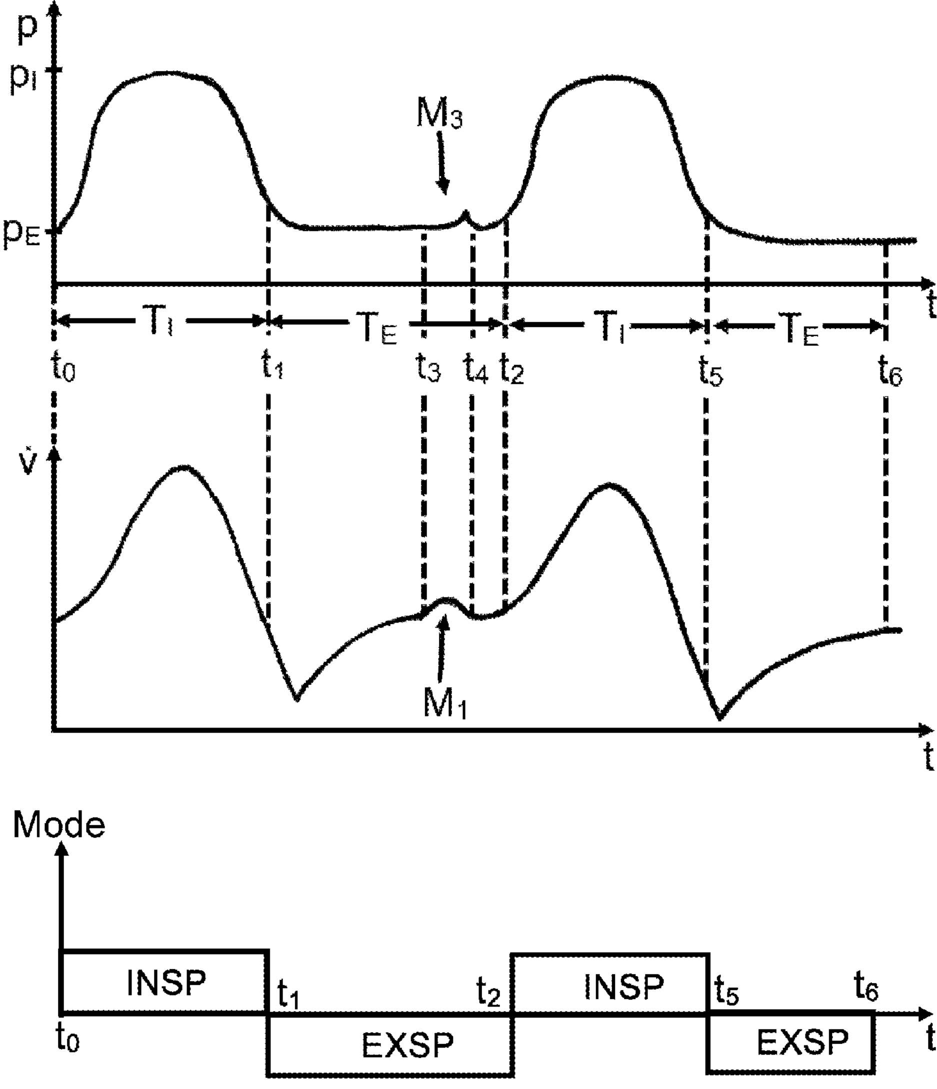
Figure 5:
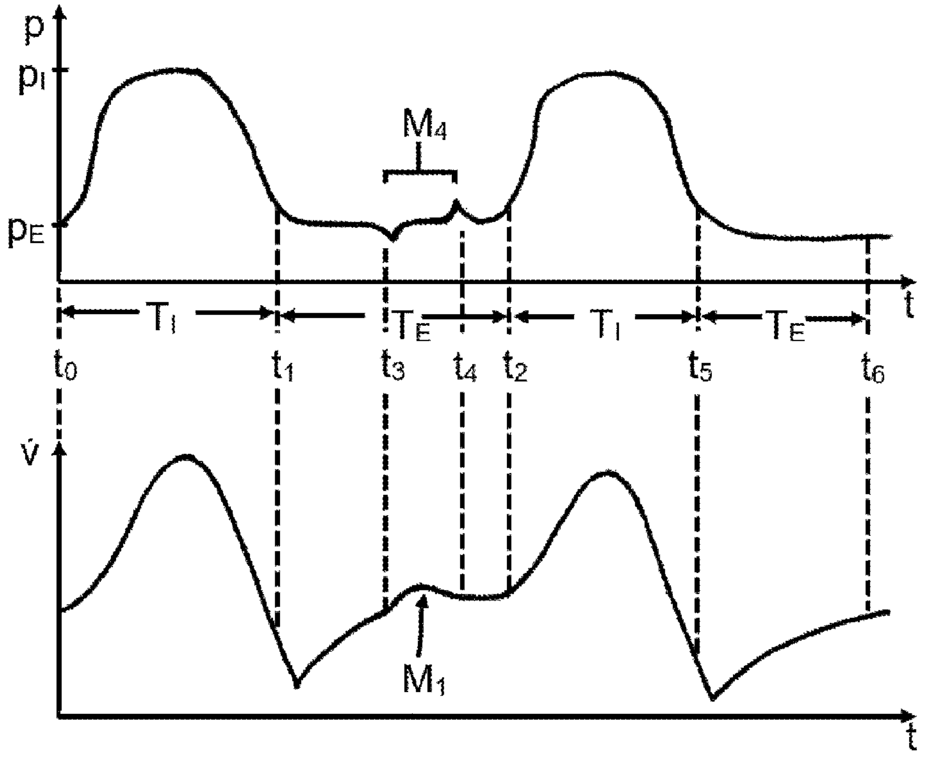
Figure 5:
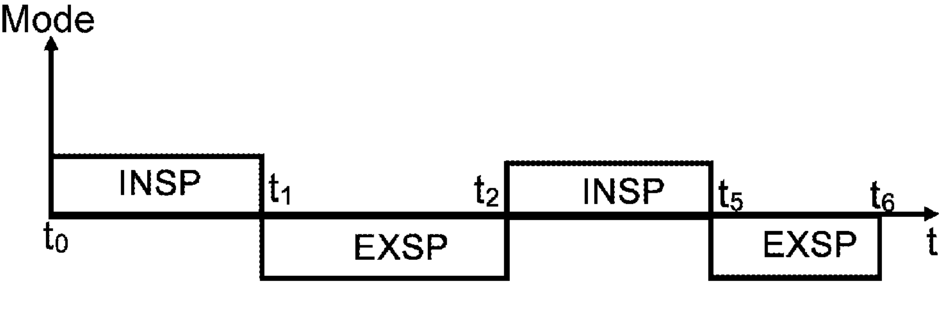

FIGS. 3 to 5 show respiratory air pressure curves and respiratory air flow curves, each with a breathing cycle consisting of the modes INSP and EXSP with a frustrated breathing movement, and, for comparison, a subsequent breathing cycle without a frustrated breathing movement. The curves shown here have different characteristic features or feature combinations $M_1$ to $M_4$ for frustrated breathing movements of the living being 3. It should be noted that the characteristic features or feature combinations $M_1$ to $M_4$ shown here are highly schematic in order to enhance understanding, and they only represent selected examples of features that have already been identified in tests as being characteristic.

In FIGS. 3 to 5, the first breathing cycle, which has a frustrated breathing movement, in each case begins at the time point $t_0$ and ends at the time point $t_2$. The change from an inspiration phase $T_I$ to an expiration phase $T_E$ of the living being 3 takes place at the time point $t_1$. Between the time points $t_3$ and $t_4$, a characteristic feature $M_1$, $M_2$, $M_3$, $M_4$ occurs in the respiratory air pressure curve and/or respiratory air flow curve. The second breathing cycle, which has no frustrated breathing movement, in each case begins at the time point $t_2$ and ends at the time point $t_6$. The change from an inspiration phase $T_I$ to an expiration phase $T_E$ of the living being 3 takes place at the time point $t_5$.

It can be seen in FIG. 3 that, within the expiration phase $T_E$ during the increase in the respiratory air flow curve between the time points $t_3$ and $t_4$, a respiratory air flow increase, identified as a bulge, occurs as characteristic feature $M_1$. In the respiratory air pressure curve, a respiratory air pressure increase, identified as a bulge, can be seen as a further characteristic feature $M_2$ substantially at the same time as the characteristic feature $M_1$. The features $M_1$ and $M_2$ can each already be considered individually as characteristic features of a frustrated breathing movement. However, they can also form a common characteristic feature of a frustrated breathing movement and can be evaluated coherently or in relation to each other. For example, it can be specified in the programmable control unit 10 that, in the sense of a two-factor dependency, the presence of a frustrated breathing movement is inferred only when the characteristic features $M_1$ and $M_2$ occur together.

It has been found that the characteristic features $M_1$ and $M_2$ are not only characteristic of a frustrated breathing movement in general, but in particular of a frustrated breathing movement as a result of a trigger insufficiency. If the programmable control unit 10 detects a respiratory air flow increase, present as a bulge, in the respiratory air flow curve and also a substantially simultaneous respiratory air pressure increase in the form of a bulge, which preferably also have substantially the same or similar gradients and/or integrals, the control unit 10 infers the presence of a frustrated breathing movement as a result of a trigger insufficiency.

It has also been found that the characteristic features $M_1$ and $M_2$ are not only characteristic of a trigger insufficiency, but in particular of a leakage-related trigger insufficiency. The trigger insufficiency shown is thus caused by leakages or by correction values, insufficiently determined by the programmable control unit 10, for taking account of leakage values such as mask leakages or technical leakages and can be reduced or avoided independently by the programmable control unit 10 by appropriate countermeasures.

It can be seen in FIG. 4 that, within the expiration phase $T_E$ of the respiratory air flow curve, during the increase in the respiratory air flow between the time points $t_3$ and $t_4$, a respiratory air flow increase, identified as a bulge, occurs as characteristic feature $M_1$. In the respiratory air pressure curve, a respiratory air pressure increase, identified as a peak, can be seen as a further characteristic feature $M_3$ between the time points $t_3$ and $t_4$, close in time to $t_4$. The features $M_1$ and $M_3$ can already individually represent characteristic features of a frustrated breathing movement. However, they can also form a common characteristic feature of a frustrated breathing movement and can be evaluated coherently or in relation to each other. For example, it can be specified in the programmable control unit 10 that, in the sense of a two-factor dependency, the presence of a frustrated breathing movement is inferred only when the characteristic features $M_1$ and $M_3$ occur together.

It has been found that the characteristic features $M_1$ and $M_3$ are not only characteristic of a frustrated breathing movement in general, but in particular of a frustrated breathing movement as a result of an intrinsic PEEP of the living being 3. If the programmable control unit 10 detects a respiratory air flow increase, present as a bulge, in the respiratory air flow curve and also a respiratory air pressure increase that occurs simultaneously or during a second half of the respiratory air flow increase and is shaped as a peak, wherein the respiratory air pressure increase preferably has a smaller integral over the time of the increase than the respiratory air flow increase, the control unit 10 infers the presence of a frustrated breathing movement as a result of an intrinsic PEEP.

It can be seen in FIG. 5 that, within the expiration phase $T_E$ of the respiratory air flow curve, during the increase in the respiratory air flow between the time points $t_3$ and $t_4$, a respiratory air flow increase, identified as a bulge, occurs as characteristic feature $M_1$. In the respiratory air pressure curve, a respiratory air pressure reduction, identified as a peak, can be seen in the first half of the time span between the time points $t_3$ and $t_4$, and a respiratory air pressure increase, identified as a peak, occurs as common characteristic feature $M_4$ in the second half of the time span between time points $t_3$ and $t_4$. The features $M_1$ and $M_4$ can already individually represent characteristic features of a frustrated breathing movement. However, they can also form a common characteristic feature of a frustrated breathing movement and can be evaluated coherently or in relation to each other. For example, it can be specified in the programmable control unit 10 that, in the sense of a two-factor dependency, the presence of a frustrated breathing movement is inferred only when the characteristic features $M_1$ and $M_4$ occur together.

It has been found that the characteristic features $M_1$ and $M_4$ are not only characteristic of a frustrated breathing movement in general, but in particular of a frustrated breathing movement as a result of a trigger insufficiency. If the programmable control unit 10 detects a respiratory air flow increase, present as a bulge, in the respiratory air flow curve and also, during the first half of the time span between the time points $t_3$ and $t_4$, a respiratory air pressure reduction, identified as a peak, and, in the second half of the time span between the time point $t_3$ and $t_4$, a respiratory air pressure increase, identified as a peak, wherein the respiratory air pressure increases preferably each have a smaller integral over the time of the increase than the respiratory air flow increase, the control unit 10 infers the presence of a frustrated breathing movement as a result of a trigger insufficiency.

It has also been found that the characteristic features $M_1$ and $M_4$ are characteristic not only of a trigger insufficiency, but in particular of a parameter-related trigger insufficiency. Thus, the trigger insufficiency shown is caused by the programmable control unit 10 predefining parameter values for sensitivity settings of the inspiration and/or expiration trigger and can be reduced or avoided, through appropriate countermeasures, independently by the control unit 10 or by external correction inputs.

Figure 6:
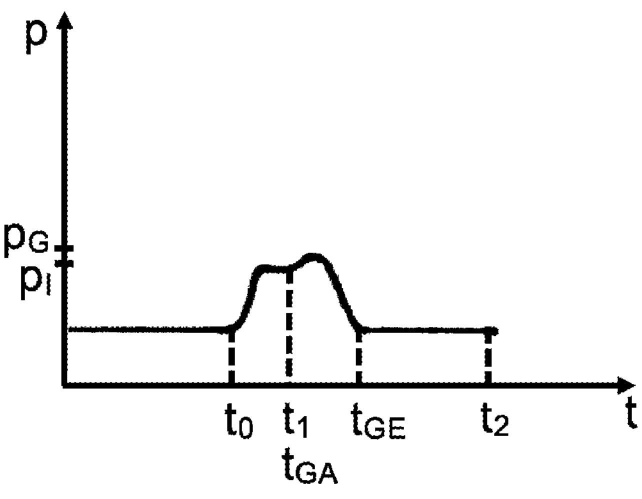
FIGS. 6-8 show respiratory air pressure curves over time during a breathing cycle with an activated deflation function of the device.
Figure 7:
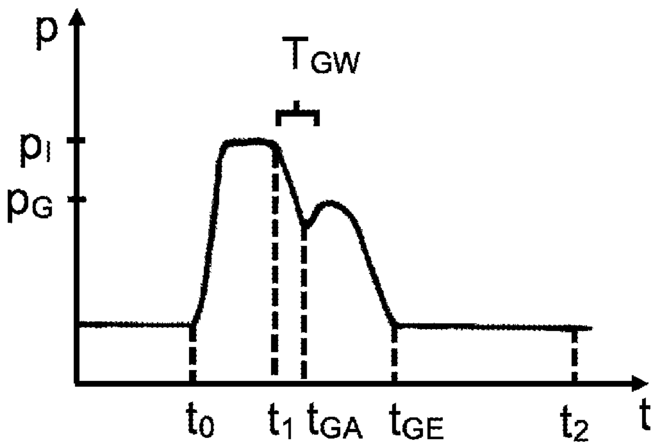
Figure 8:
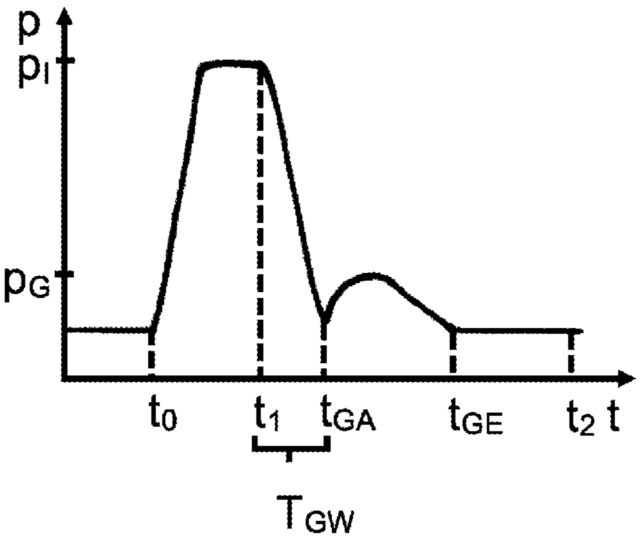

FIGS. 6 to 8 show, by way of examples, respiratory air pressure curves over time during a breathing cycle with an activated deflation function of the device 1. In this case, in the expiration phase $T_E$ of the breathing cycle, the device 1 generates a counterpressure which provides the living being 3 with breathing resistance and thereby enables more comfortable exhalation and prevents collapse of the airways. The breathing cycle begins at the time point $t_0$ with an increase in the respiratory air pressure to the IPAP value $p_I$. At the time point $t_1$ the inspiration ends, and the expiration begins that ends at the time point $t_2$. Between the time points $t_1$ and $t_2$, i.e. during the expiration, the device 1 generates a counterpressure.

The counterpressure is controlled, in particular dynamically, from a counterpressure start time $t_{GA}$ to a counterpressure end time $t_{GE}$. A maximum counterpressure, the counterpressure amplitude $p_G$, is reached between the time points $t_{GA}$ and $t_{GE}$.

In FIG. 6, this counterpressure is already generated with the start of the expiration at the time point $t_1$, that is to say without a counterpressure wait time after the time point $t_1$. In FIGS. 7 and 8, initiation of the counterpressure generation is delayed, so that there is a time difference between the time point $t_1$ and the time point $t_{GA}$. This time difference is designated as the counterpressure wait time $T_G$W. In FIG. 8, the counterpressure wait time $T_{GW}$ is set longer than in FIG. 7. In addition, the levels of the IPAP values $p_I$ and the counterpressure amplitudes $p_G$ in FIGS. 6 to 8 are chosen to be different. The counterpressure parameters of the counterpressure generated by the device 1 are thus variably adjustable, predefined by the programmable control unit 10 and/or dynamically adaptable to the respiratory air flow of the living being 3. The counterpressure parameters include, in particular, the counterpressure wait time $T_{GW}$, the counterpressure amplitude $p_G$, and counterpressure rise and fall times. The counterpressure wait time $T_{GW}$ is the time span between the time point of the change from an inspiration phase to an expiration phase and the start of the counterpressure build-up generated by the device 1. The counterpressure amplitude $p_G$ describes the maximum pressure value of the counterpressure above the pressure value that prevails at the time point $t_1+T_{GW}$ at which no counterpressure is yet generated by the device 1. The counterpressure amplitude $p_G$ is preferably chosen as a function of the counterpressure wait time $T_{GW}$. Furthermore, the counterpressure wait time $T_{GW}$ is preferably chosen as a function of the level of the IPAP value $p_I$. The counterpressure curve over time can vary in order to meet the individual needs of the living being 3 for breathing resistance. Thus, for example, the counterpressure curve in FIG. 8 has a less steep counterpressure fall time compared to the counterpressure curve in FIG. 6 or 7. The counterpressure parameters are preferably automatically regulated by the programmable control unit 10 in such a way that the occurrence of frustrated breathing movements is avoided or at least reduced, by the control unit 10 varying the counterpressure parameters in a suitable manner when frustrated breathing movements are detected on the basis of characteristic features.

Figure 9:
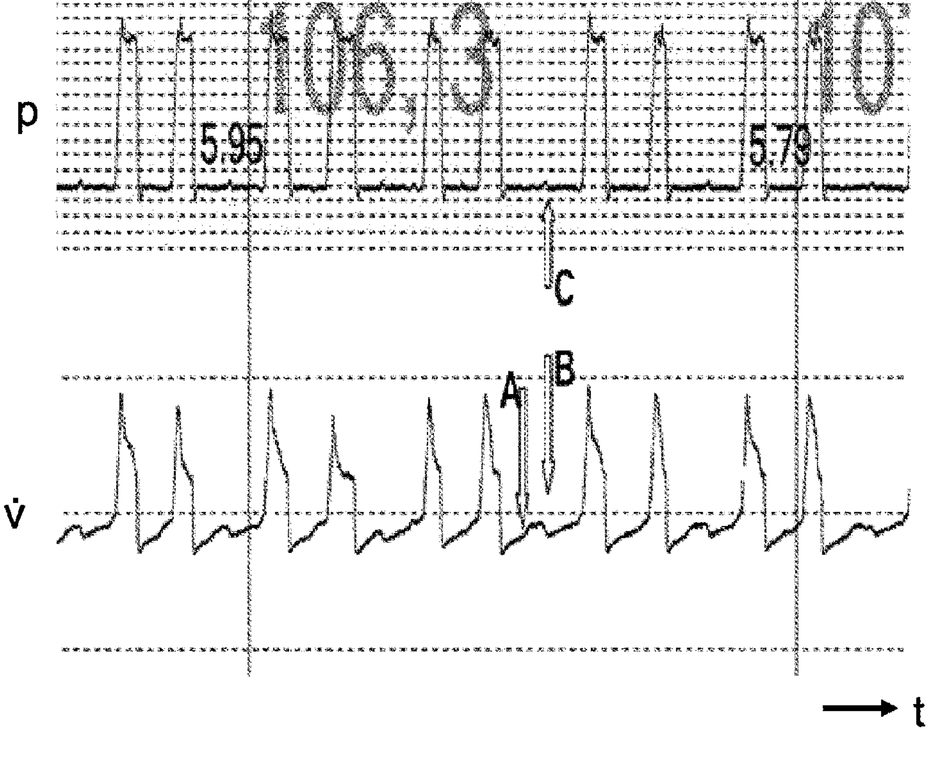
FIG. 9 shows an actually recorded respiratory air pressure curve and respiratory air flow curve with detectable frustrated breathing movements.

FIG. 9 shows a respiratory air pressure curve and respiratory air flow curve, actually recorded on the basis of measured values of a living being 3, with detectable frustrated breathing movements. The upper diagram shows the respiratory air pressure curve, and the lower diagram shows the respiratory air flow curve. It will be seen that, in the respiratory air flow curve, respiratory air flow increases, which are present as bulges, repeatedly occur in the expiration phase of the living being 3. By way of example, the temporal beginning and the temporal end of the respiratory air flow increase in a breathing cycle are indicated by the arrows A and B. In the respiratory air pressure curve, respiratory air pressure increases, identified as peaks, are repeatedly detected, the peaks of the respiratory air pressure increases being clearly smaller than the respiratory air flow increases that are identified as bulges. In addition, the respiratory air pressure increases occur temporally at the end of the respiratory air flow increases that are present as bulges, as can be seen for the breathing cycle selected as an example and indicated by the arrow C, which characterizes the occurrence of the respiratory air pressure increase. On the basis of the temporal relationship of the respiratory air flow increases and of the respiratory air pressure increases to each other, and on the basis of the forms of the respective increase, it is possible in the case of FIG. 9 to infer the presence of a frustrated breathing movement on account of an intrinsic PEEP.

The invention claimed is:

1. A device for supportive ventilation of a living being, comprising:

a sensor arrangement, a programmable control unit, and an air delivery unit controllable by the programmable control unit, wherein the sensor arrangement comprises a pressure sensor and an air flow sensor which are respectively designed for temporally successive detection of respiratory air pressure values of the living being and temporally successive detection of respiratory air flow values of the living being over one or more respiratory cycles, wherein the programmable control unit is designed to evaluate respiratory air pressure curves and respiratory air flow curves formed from the temporally successive respiratory air pressure values and the temporally successive respiratory air flow values detected by the sensor arrangement, by an evaluation configured to include identifying characteristic features of the respiratory air flow curves and characteristic features of the respiratory air pressure curves, which are characteristic of frustrated breathing movement, wherein the programmable control unit is further designed to detect frustrated breathing movements of the living being by a detecting based on a combination of the identified characteristic features of the respiratory air pressure curves and the identified characteristic features of the respiratory air flow curves, the detecting being configured to indicate detection of a detected frustrated breathing movement based at least in part on detecting at least one of the identified characteristic features of the respiratory air pressure curves being related, at least temporally, to at least one of the identified characteristic features of the respiratory air flow curves, wherein the detecting is further configured to include distinguishing of the detected frustrated breathing between being:

a frustrated breathing movement occurring as a result of an intrinsic PEEP of the living being, and a frustrated breathing movement occurring as a result of a trigger insufficiency, and wherein the detecting of the detected frustrated breathing movement and the distinguishing of the frustrated breathing movement are performed based on evaluation of the relation between the respiratory air pressure and respiratory air flow curves measured for the same breath, without requiring comparison of the respiratory air pressure or air flow curves with stored abnormal reference waveforms, and wherein the distinguishing is based at least in part on a shape feature of the at least one of the identified characteristic features of the respiratory air pressure curves that the detecting determined as being related, at least temporally, to the at least one of the identified characteristic features of the respiratory air flow curves.

2. The device as claimed in claim 1, wherein:

the characteristic features of the respiratory air pressure curves comprise maxima, minima, bulges, turning points, saddle points, amplitudes, integrals, and/or gradients or derivatives at predefined time points and/or time segments of the respiratory air pressure curves, and the characteristic features of the respiratory air flow curves comprise maxima, minima, bulges, turning points, saddle points, amplitudes, integrals, and/or gradients or derivatives at predefined time points and/or time segments of the respiratory air flow curves.

3. The device as claimed in claim 1 wherein the characteristic features of the respiratory air pressure curves comprise characteristic deviations from predefined reference respiratory air pressure curves and/or the characteristic features of the respiratory air flow curves comprise characteristic deviations from predefined reference respiratory air flow curves.

4. The device as claimed in claim 1 wherein the programmable control unit comprises a memory unit for storing predefined reference respiratory air pressure curves and/or predefined reference respiratory air flow curves and/or reference features for characteristic features of frustrated breathing movements.

5. The device as claimed in claim 4, wherein the memory unit has various disease-specific reference respiratory air pressure curves and/or various disease-specific reference respiratory air flow curves and/or various disease-specific reference features for characteristic features of frustrated breathing movements.

6. The device as claimed in claim 1 wherein the programmable control unit is further designed such that the distinguishing of the detected frustrated breathing movement as being a frustrated breathing movement occurring as a result of a trigger insufficiency includes further distinguishing, based on the at least one of the identified characteristic features of the respiratory air flow curves and the shape feature of the at least one of the identified characteristic features of the respiratory air pressure curves determined as being related, at least temporally, to the at least one of the identified characteristic features of the respiratory air flow curves, the detected frustrated breathing movement between being a frustrated breathing movement occurring as a result of a leakage-related trigger insufficiency and a frustrated breathing movement occurring as a result of a parameter-related trigger insufficiency.

7. The device as claimed in claim 1 wherein the programmable control unit is further designed to perform detection of at least one of the frustrated breathing movements based at least in part on a time point, a time span, and/or a form of a respiratory air pressure increase or reduction and/or a respiratory air flow increase or reduction, appearing in the respiratory air pressure curves and/or in the respiratory air flow curves.

8. The device as claimed in claim 1 wherein the programmable control unit is further designed to perform oscillometric airway resistance measurements.

9. The device as claimed in claim 1 wherein the programmable control unit is further designed to:

determine, based on instances wherein a result of the distinguishing is that the detected frustrated breathing movement is a frustrated breathing movement occurring as a result of an intrinsic PEEP of the living being, a frequency and/or an intensity of the intrinsic PEEP of the living being, and/or determine, based on instances wherein a result of the distinguishing is that the detected frustrated breathing movement is a frustrated breathing movement occurring as a result of a trigger insufficiency, a frequency and/or an intensity of the trigger insufficiency.

10. The device as claimed in claim 9, wherein the programmable control unit is further designed to output an acoustic, optical and/or haptic alarm signal when a predefined threshold value for the frequency and/or the intensity of the intrinsic PEEP or of the trigger insufficiency is exceeded.

11. The device as claimed in claim 1 wherein the programmable control unit is further designed to automatically vary control parameters of the air delivery unit in response to detection of one or more of the frustrated breathing movements.

12. The device as claimed in claim 11, wherein the programmable control unit is further designed for continuous regulating automatic variation of control parameters of the air delivery unit, in a manner to reduce and/or eliminate occurrences of the characteristic features of the respiratory air pressure curves and/or occurrences of the characteristic features of the respiratory air flow curves.

13. The device as claimed in claim 11 wherein the programmable control unit is further designed to automatically vary control parameters of the air delivery unit in a manner to reduce occurrences of the characteristic features of the respiratory air pressure curves and/or reduce occurrences of the characteristic features of the respiratory air flow curves, according to a predefined intrinsic minimum PEEP.

14. The device as claimed in claim 13, wherein the programmable control unit is further designed to determine the predefined intrinsic minimum PEEP on the basis of pCO2 measurements.

15. The device as claimed in claim 11 wherein a control parameter predefined by the programmable control unit functions as an inspiration trigger or an expiration trigger for changing the device from an inspiration mode to an expiration mode, or vice versa.

16. The device as claimed in claim 11 wherein a control parameter predefined by the programmable control unit functions as a respiratory air pressure curve and/or a respiratory air flow curve of air delivered by the air delivery unit.

17. The device as claimed in claim 11 wherein a control parameter predefined by the programmable control unit functions as a counterpressure and/or a counterpressure curve and/or a counterpressure amplitude and/or a counterpressure wait time during the expiration phase.

18. The device as claimed in claim 17, wherein the counterpressure amplitude and/or the counterpressure wait time is settable as a function of each other and/or as a function of an IPAP value or a IPAP value range and/or as a function of a differential pressure of IPAP to EPAP.

19. The device as claimed in claim 1 wherein the programmable control unit is further designed such that based on distinguishing of a detected frustrated breathing movement occurring as a result of an intrinsic PEEP of the living being, the programmable control unit automatically reduces a backup frequency and/or reduces an IPAP value and/or reduces a maximum inspiration time to automatically increase an expiration trigger sensitivity after elimination of a detected frustrated breathing movement occurring as a result of an intrinsic PEEP of the living being, and/or the programmable control unit automatically increases the backup frequency and/or increases the IPAP value and/or increases the maximum inspiration time to automatically reduce the expiration trigger sensitivity after elimination of a detected frustrated breathing movement occurring as a result of the intrinsic PEEP of the living being.

20. The device as claimed in claim 1 wherein the programmable control unit comprises a pattern recognition unit designed for recognizing characteristic features of the respiratory air pressure curves and/or the characteristic features of the respiratory air flow curves.

21. A computer program with program code encoded on a non-transient storage medium-designed to carry out a method for supportive ventilation of a living being with a ventilator when the computer program is executed on a computing unit of the ventilator, wherein a pressure sensor and an air flow sensor of the ventilator respectively detect temporally successive respiratory air pressure values of the living being and temporally successive respiratory air flow values of the living being over one or more respiratory cycles, wherein a programmable control unit of the ventilator evaluates respiratory air pressure curves and respiratory air flow curves formed from the temporally successive respiratory air pressure values and the temporally successive respiratory air flow values detected by the pressure sensor and the air flow sensor, by an evaluation that includes identifying characteristic features of the respiratory air pressure curves, which are characteristic of frustrated breathing movement, and characteristic features of the respiratory air flow curves, which are characteristic of frustrated breathing movement, and wherein the programmable control unit of the ventilator indicates a detected frustrated breathing movement of the living being based at least in part on detecting at least one of the identified characteristic features of the respiratory air pressure curves being related, at least temporally, to at least one of the identified characteristic features of the respiratory air flow curves, and associated with indicating the detected frustrated breathing movement, the distinguishes the detected frustrated breathing movement between being:

a frustrated breathing movement occurring as a result of an intrinsic PEEP of the living being, and a frustrated breathing movement occurring as a result of a trigger insufficiency, by a distinguishing that is based at least in part on a shape feature of the least one of the identified characteristic features of the respiratory air pressure curves detected as related, at least temporally, to the at least one of the identified characteristic features of the respiratory air flow curves.

22. The device as claimed in claim 7 wherein the programmable control unit is further designed such that distinguishing of a detected frustrated breathing movement between being a frustrated breathing movement occurring as a result of an intrinsic PEEP of the living being and a frustrated breathing movement occurring as a result of a trigger insufficiency is further based on the time point, the time span and/or the form of the respiratory air pressure increase or reduction and/or the respiratory air flow increase or reduction in the respiratory air pressure curves and/or the respiratory air flow curves.

23. The device as claimed in claim 1, wherein the distinguishing of a detected frustrated breathing movement between being a frustrated breathing movement occurring as a result of an intrinsic PEEP of the living being and a frustrated breathing movement occurring as a result of a trigger insufficiency comprises determining a respective temporal relation between a respective time of one of the identified characteristic features of the respiratory air pressure curves and a respective time of one of the identified characteristic features of the respiratory air pressure curves.

* * * * *